United States Patent [19]

Friedman

[11] Patent Number: 4,599,900

[45] Date of Patent: Jul. 15, 1986

[54] WORKPIECE FOR HANDLING APPARATUS FOR NONDESTRUCTIVE TESTING

[75] Inventor: Gary Friedman, Reseda, Calif.

[73] Assignee: Automation Industries, Inc., Greenwich, Conn.

[21] Appl. No.: 567,566

[22] Filed: Jan. 3, 1984

[51] Int. Cl.⁴ .......................................... G01N 29/04
[52] U.S. Cl. .................................................... 73/622
[58] Field of Search ................. 73/618, 619, 620, 621, 73/622, 633, 637, 638, 640

[56] References Cited

U.S. PATENT DOCUMENTS

| | | | |
|---|---|---|---|
| 3,077,769 | 2/1963 | Rankin | 73/622 |
| 3,981,184 | 9/1976 | Matay | 73/622 |
| 4,055,989 | 11/1977 | Henry et al. | 73/638 |
| 4,434,659 | 3/1984 | Kurtz et al. | 73/633 |

FOREIGN PATENT DOCUMENTS

| | | | |
|---|---|---|---|
| 2338658 | 2/1975 | Fed. Rep. of Germany | 73/622 |
| 0111881 | 9/1979 | Japan | 73/637 |
| 0824013 | 4/1981 | U.S.S.R. | 73/637 |

*Primary Examiner*—S. Leon Bashore
*Assistant Examiner*—Andrew J. Anderson
*Attorney, Agent, or Firm*—Thomas L. Flattery

[57] ABSTRACT

First and second pairs of rollers are adjustably positionable along a pair of guide tubes within a fluid-filled tank in aligned, end spaced relation. A cylindrical workpiece resting within the interstices of the two pairs of rollers is incrementally rotated by an electro-hydraulic step motor. A sonic transducer scans the workpiece longitudinally with the workpiece being rotatively indexed successively after each scan.

5 Claims, 5 Drawing Figures

WORKPIECE FOR HANDLING APPARATUS FOR NONDESTRUCTIVE TESTING

The present invention relates generally to nondestructive testing of elongated workpieces, and, more particularly, to apparatus for supporting and indexing the workpiece with respect to a scanning head in an ultrasonic nondestructive test system.

BACKGROUND

In the nondestructive testing of elongated relatively large and bulky parts by ultrasonic techniques, the part (workpiece) to be tested is located within a fluid bath (e.g., water) and a transducer is caused to scan from one end to the other of the part. On each scanning traversal of the ultrasonic transducer, the workpiece is rotated so that a different line of test may be achieved. Typically, the test information is stored for later use and evaluation, or the workpiece itself is marked at each defect location.

SUMMARY OF THE DISCLOSURE

In accordance with the described invention there is provided and open-top tank containing a supply of a fluid, such as water, which readily conducts ultrasonic energy and which is of such a size as to enable receipt in a completely immersed manner, the workpiece to be tested and apparatus for incrementally rotating the workpiece. Ultrasonic generating and detecting means are located within the tank and closely spaced to the workpiece with means for moving a sonic transducer and detector along the full length of the workpiece.

The workpiece has one end portion resting on a pair of rollers, one a drive roller and the other an idler roller, and the other end portion on a pair of idler rollers. The power source for providing an incremental rotation to the workpiece at the end of each longitudinal scan consists of a combination hydraulic and electrical step motor which provides an output shaft rotation on each impulse of a precise predetermined angular extent and with high torque. The hydraulic-electrical power source is located within a housing that is sealed and includes a quantity of hydraulic fluid in surrounding relationship to the various parts for full electrical isolation.

A drive shaft extending outwardly of the power source housing includes a toothed pulley by which a drive belt interconnects to a single relatively short drive roller. A second relatively short idler roller is located on a common support means closely adjacent to the first roller and includes an enlarged flange member serving as an end stop for the workpiece. The associated drive idler rollers and power source are mounted on a plate which can be adjustably positioned along a pair of guide tubes located in the test tank and extending parallel to the line of scan.

A further set of rollers consisting of first and second idler rollers are aligned, respectively, with the first described drive and idler rollers. More particularly, the further idler rollers are unitarily mounted on a plate which is adjustably positionable on the guide tubes at any suitable longitudinal spacing from the first described drive and idler rollers.

In use, the further pair of idler rollers are positioned with respect to the first described pair of drive and idler rollers so as to accommodate the workpiece length. The workpiece is then located onto the rollers by the use of a hoist or other such means, and the test operation begins with the scanning nondestructive testing of a first line or segment of the workpiece. Next, incremental rotation of the workpiece is provided and a further line or segment is tested. This is continued until the entire workpiece has been tested or other prescribed number of tests have been accomplished.

DESCRIPTION OF A PREFERRED EMBODIMENT

Figure 1:
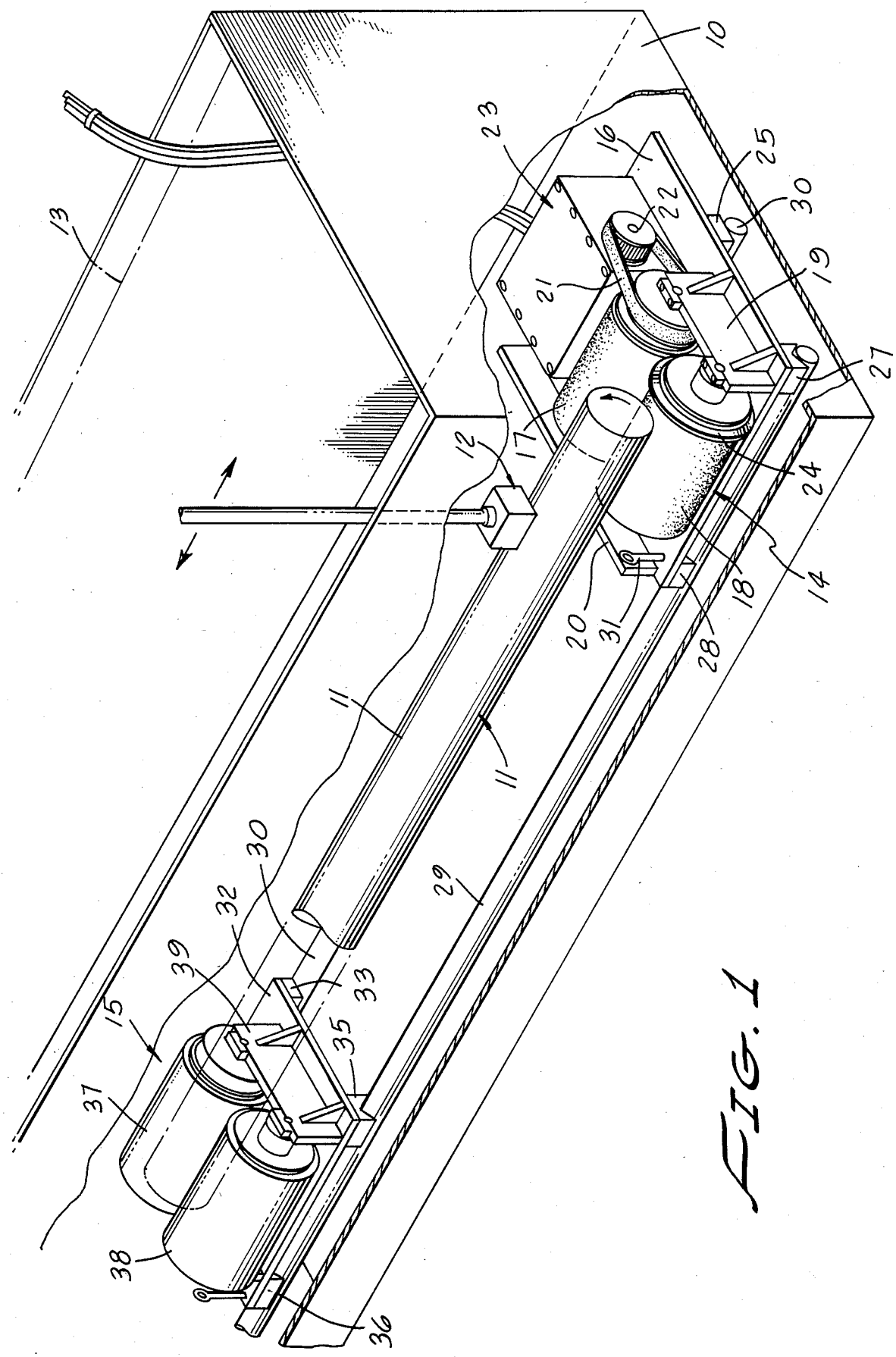
FIG. 1 is a perspective partially fragmentary view of the testing tank, testing apparatus and workpiece incremental drive means.

With reference now to the drawing and particularly FIG. 1, there is shown a generally rectangular, open-top tank 10 within which a cylindrical workpiece 11 is selectively rotated during scanning by an ultrasonic transducer identified generally as at 12. More particularly, in a way that will be described in detail, the workpiece 11 is scanned by the transducer 12 moving longitudinally therealong with ultrasonic vibrations being transmitted to the workpiece via the fluid 13 which, in a way well known in the art, serves to identify defects in the workpiece. After a single line or segment is tested by the scanning transducer, an incremental rotating power drive apparatus to be described indexes the workpiece a predetermined angular extent and the transducer scans a new line for defects.

Typically, ultrasonic test means include an ultrasonic transducer such as a piezoelectric element which upon being impulsed by an electric signal produces sonic vibrations which are propagated through the fluid 13 to impinge upon the workpiece 11 and reflected back to a monitoring means. The vibrating surface is maintained at a fixed, predetermined spacing to the surface of the workpiece and at all times a continuous layer of fluid 13 is maintained therebetween and in contact with both. In a way well known in the art, variations in the time spacing and character of reflected ultrasonic energy provides indications of defects existing in the workpiece. A defect location can be either noted by monitoring the relative location of the scanning transducer head with respect to the workpiece and providing the electronic signal on a defect being noted, or a suitable identification mark can be applied directly to the workpiece at the defect location. All of this is well known in the art and for that reason sonic testing and marking equipment specifics and use are not provided.

With respect to the more general aspects of incremental angular drive for the workpiece 11 reference is still made to FIG. 1 where it is seen that one end portion of the workpiece is received in the space between a first pair of rollers on a drive assembly 14 while the other workpiece end portion is received on a support assembly 15 including a pair of idler rollers. The assemblies 14 and 15 are precisely arranged so that the workpiece 11 will remain at the same spatial relation to the transducer 12 as the latter moves longitudinally of the workpiece during test.

Figure 2:
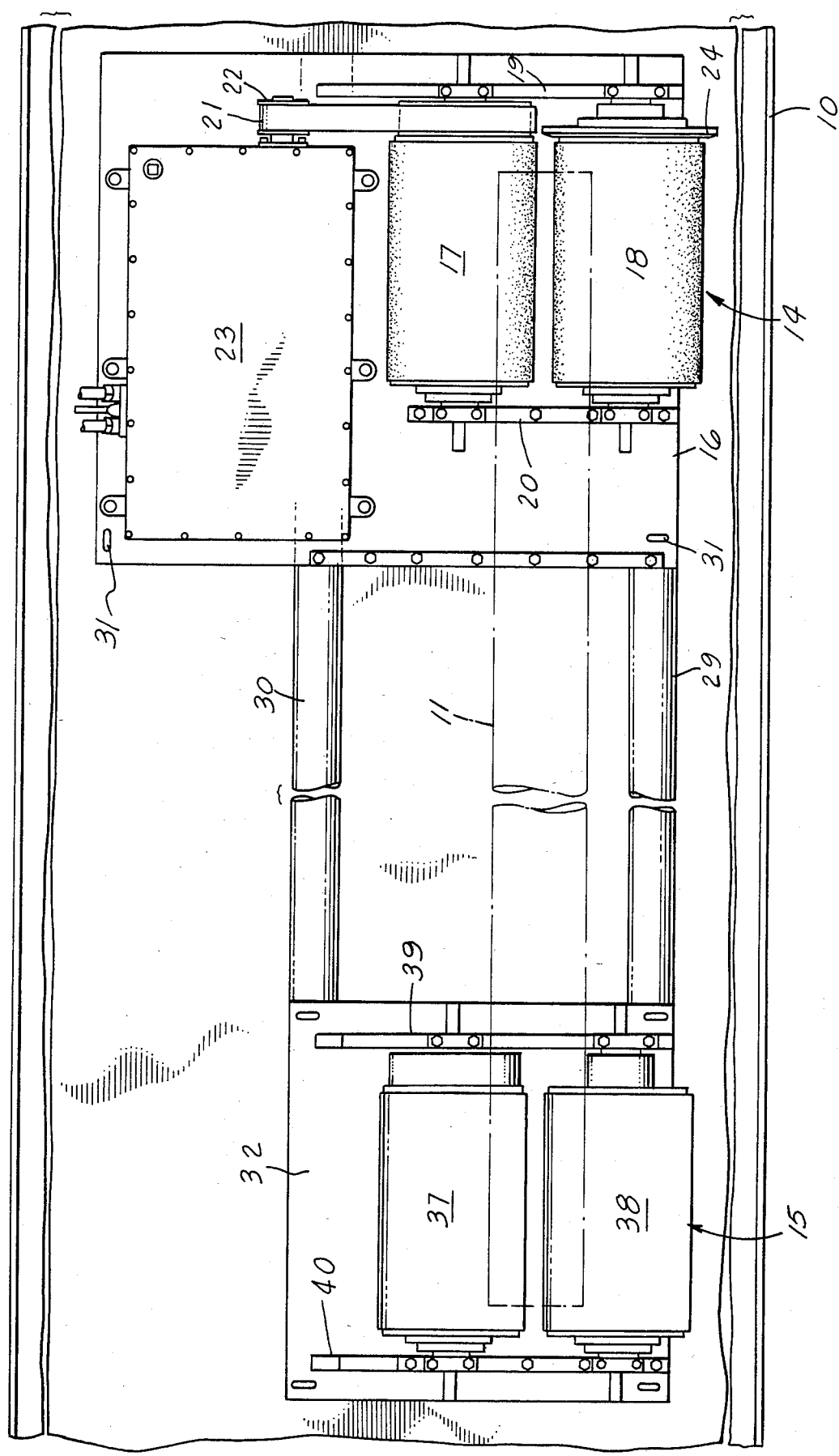
FIG. 2 is a plan elevational view of the apparatus of FIG. 1.
Figure 3:
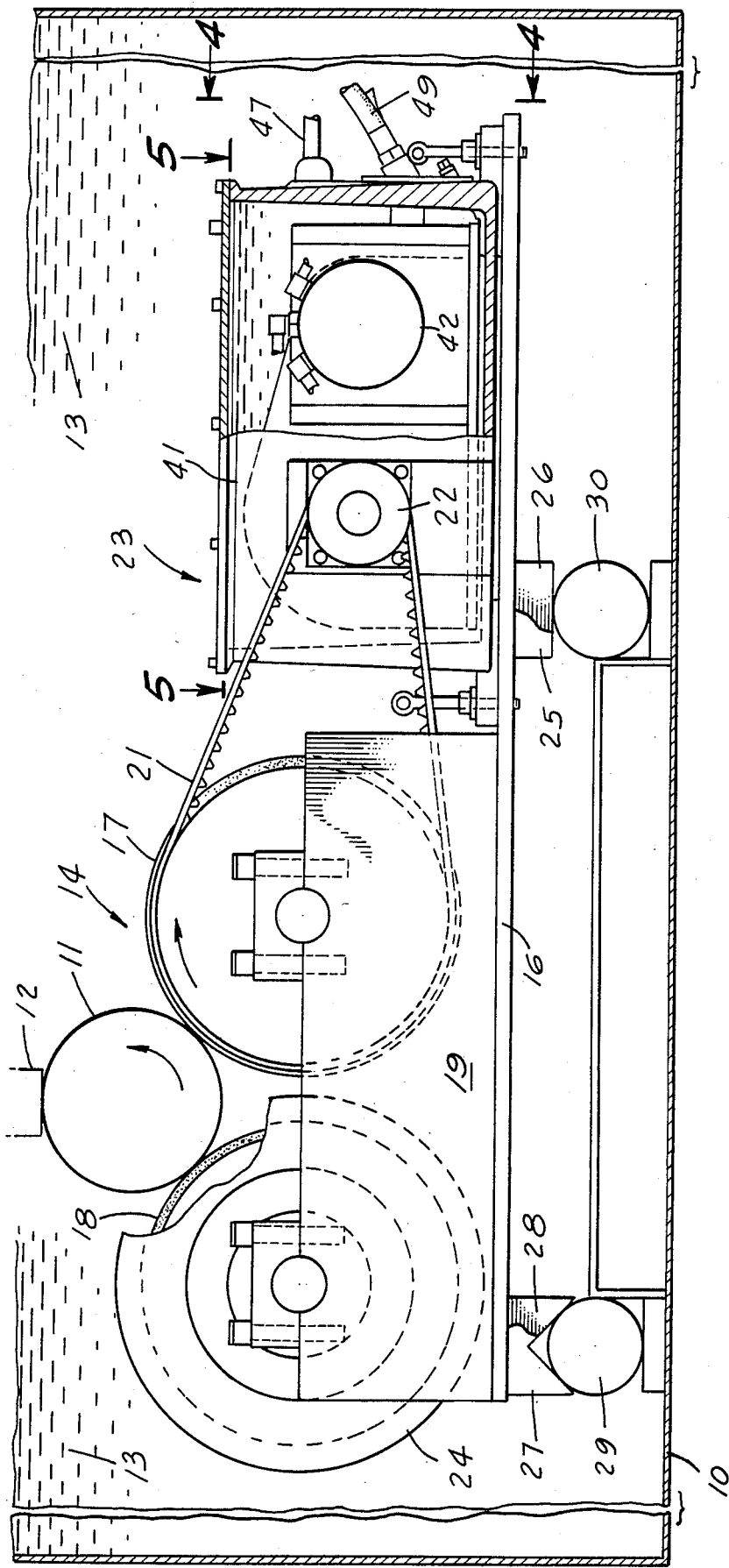
FIG. 3 is an end elevational, sectional view shown looking into the driven end of the workpiece.
Figure 4:
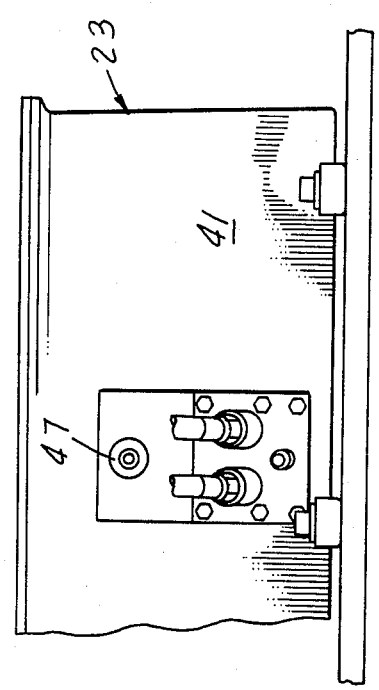
FIG. 4 is a back, partially fragmentary, elevational view taken along the line 4—4 of FIG. 3.

For the ensuing detailed description of the drive assembly 14 reference is made to both FIGS. 1 and 2. The assembly parts are mounted on the upper surface of a generally rectangular plate 16. More particularly, first and second rollers 17 and 18 are respectively journaled in a pair of separated upstanding wall members 19 and 20 affixed to the upper surface of plate 16. A reduced diameter end portion of the first or drive roller 17 is toothed for co-acting with a belt 21 that similarly meshes with a drive pulley 22 extending outwardly from a rotational power source 23 to be described. The second roller 18 is an idler roller maintained laterally spaced from drive roller 17. An enlarged flange 24 on the second roller 18 serves as an end stop to prevent the workpiece from being longitudinally moved off the rollers during rotation.

The lower surface of the plate 16 includes first and second flat-surfaced feet 25 and 26 arranged along an axis parallel to the rotational axes of the drive rollers 17 and 18. V-block mounting feet 27 and 28 are also mounted on the lower surface of plate 16 with their V-shaped surfaces downwardly facing and aligned parallel to the axis of the feet 25 and 26 and spaced therefrom. By these feet 25-28, the plate 16 and all the apparatus mounted on it can be unitarily positioned along a pair of cylindrical guide tubes 29 and 30 mounted within the tank 10 and extending parallel to the path of movement of the transducer 12. Eye bolts 31 are provided for raising and lowering the assembly 14 off and onto the tubes 29 and 30.

The idler roller assembly 15 is similarly mounted on a generally rectangular flat plate 32, the lower surface of which includes first and second aligned V-block feet 35 and 36. As in the case of the drive assembly 14, the feet 33-36 provide for precise adjustable resting location of the assembly 15 along the guide rods 29 and 30.

Idler rollers 36 and 37 have their ends rotatably journaled into opposed parallal upstanding walls 39 and 40 affixed to the upper surface of plate 32. The rollers are mutually parallel with their circumferential surfaces slightly spaced providing a somewhat V-shaped interstice for receiving an end portion of the workpiece therewithin. The idler rollers 37 and 38, as well as rollers 17 and 18, have a smooth peripheral surface formed from a suitable resilient material such as rubber which will frictionally engage the workpiece but not damage it during test.

Figure 5:
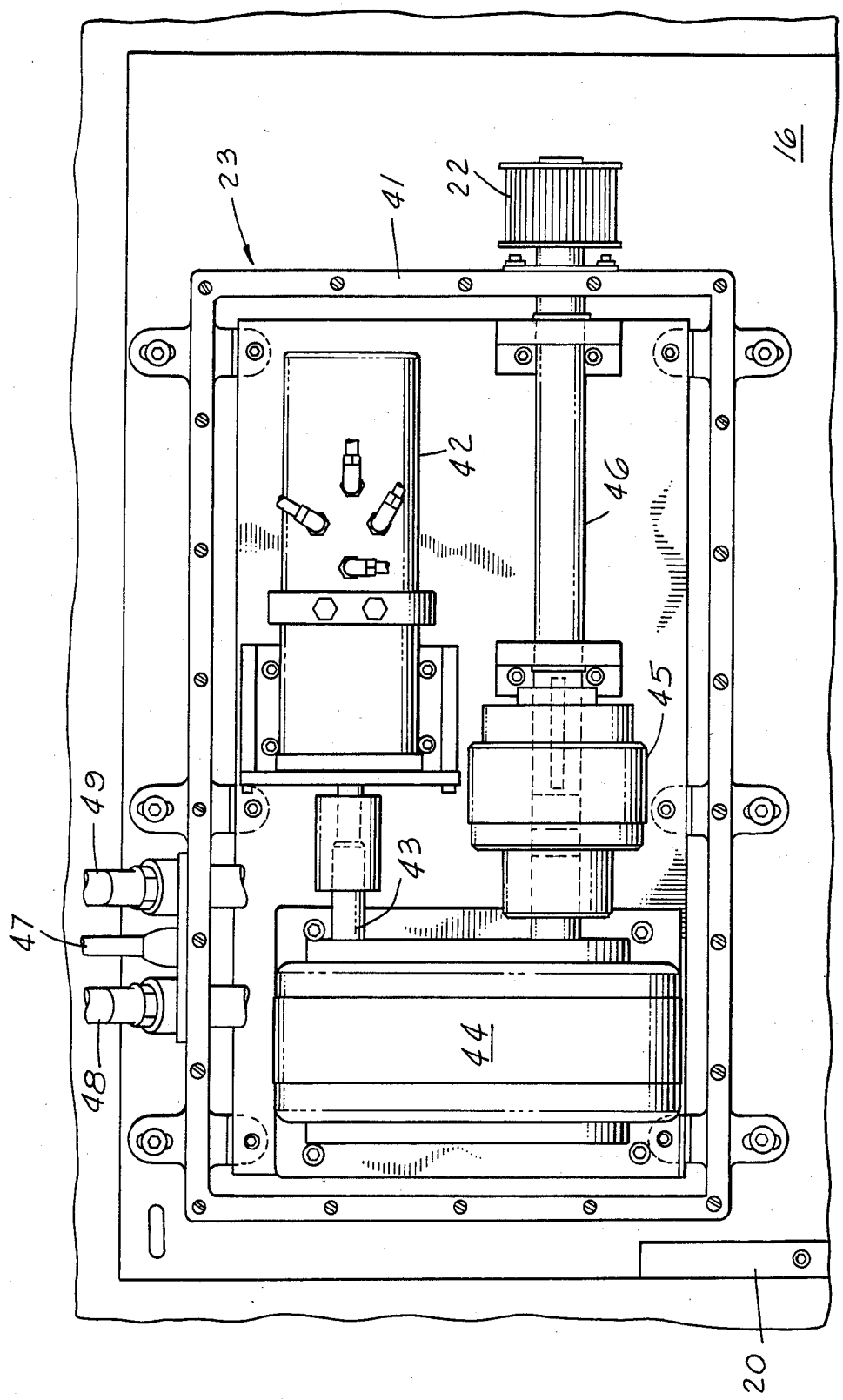
FIG. 5 is a top plan sectional view of the incremental power source taken along the line 5—5 of FIG. 3.

Turning now to FIG. 5, the rotational power source 23 includes an open-top housing 41 with a removable cover which makes the housing a liquid-proof enclosure for a purpose to be described. The basic power source consists of an electric step-motor with hydraulic torque enhancement 42 which provides rotative input via shaft 43 to a step-down gear box 44. Output of the gear box 44 interconnects via a torque limiting clutch 45 to a shaft 46 extending through the housing wall drivingly interconnected with the toothed pulley 22. Electric energization for the step-motor is provided by cabling 47 and hydraulic fluid entrance and exit by tubing 48 and 49. This power source provides high torque, controllable incremental (step) rotative power to the pulley 22, and thus to the drive roller 17 for indexing the workpiece.

In a practical construction of the invention the power source 42 consisted of an electro-hydraulic stepper motor manufactured and sold under the trade designation Model 221.10A-15D-006 by MTS Systems Corp., Minneapolis, Minn. 55424. By the described system, a workpiece up to 24 inches in diameter and weighing 20,000 pounds have been tested.

As shown in FIG. 1, the power source 23 when located in the fluid filled tank has its cover in place preventing leakage of the fluid 13 into the power source interior. Also, prior to placing the cover on the power source the housing 41 interior is filled with an electrically nonconductive liquid (e.g., hydraulic fluid) to aid in preventing electrical shorting problems and prevent corrosion from moisture build-up.

In use, the roller assemblies 14 and 15 are adjustably positioned on guide tubes 29 and 30 so as to accomodate the workpiece length. With the tank 10 filled with water the workpiece is lowered onto the two sets of rollers with its respective end portions located in the interstices between paired rollers. The sonic transducer 12 is then lowered to the proper spatial relation to the workpiece and the transducer is moved along the full workpiece length to perform one test scan. The power source 23 is then impulsed to rotate the workpiece a predetermined angular extent following which a further scan is made by the transducer. The process is repeated until the test is completed.

I claim:

1. In apparatus for nondestructive testing of an elongated workpiece by moving a vibrating surface in spaced relation to the workpiece parallel to its longitudinal axis while the vibrating surface and workpiece are immersed in a tank containing a supply of a sound wave conducting fluid, the improvement comprising;
  a first pair of workpiece support rollers mounted in the tank and located to receive and end portion of the workpiece resulting thereon;
  a second pair of rollers located in the tank to receive another end portion of the workpiece resting thereon; and
  incremental rotative power means mounted within the tank and interconnected with one of said first pair of rollers to incrementally rotate the interconnected roller and the workpiece for successively moving an adjacent workpiece peripheral surface area into opposed relation to the vibrating surface until the entire workpiece peripheral surface has been scanned by the vibrating surface.

2. Apparatus as in claim 1, in which there is further provided guide tube means along which the first and second pairs of rollers are independently adjustably positionable.

3. Apparatus as in claim 1, in which incremental rotative power means includes a toothed pulley and a toothed belt meshed with said pulley and a toothed portion of one of the first pair of rollers.

4. Apparatus as in claim 3, in which the first pair of rollers and incremental rotative power means are mounted on the upper surface of a plate having feet means for sliding receipt on the guide rod means.

5. Apparatus as in claim 1, in which the rollers of said first pair of rollers are mounted for rotation about parallel axes, and the rollers of said second pair of rollers are mounted for rotation about parallel axes and the axes of said first and second pairs of rollers are aligned.

* * * * *